United States Patent
Dwyer et al.

(10) Patent No.: US 7,276,616 B2
(45) Date of Patent: Oct. 2, 2007

(54) PHOSPHOROUS CONTAINING LIGANDS FOR METATHESIS CATALYSTS

(75) Inventors: Catherine Lynn Dwyer, Vanderbijlpark (ZA); Ann Elizabeth Catherine McConnell, Fife (GB); Grant Stephen Forman, Fife (GB)

(73) Assignee: Sasol Technology (UK) Limited, Scotland (GB)

( * ) Notice: Subject to any disclaimer, the term of this patent is extended or adjusted under 35 U.S.C. 154(b) by 29 days.

(21) Appl. No.: 10/518,716

(22) PCT Filed: Jul. 4, 2003

(86) PCT No.: PCT/ZA03/00087

§ 371 (c)(1),
(2), (4) Date: Aug. 1, 2005

(87) PCT Pub. No.: WO2004/005223

PCT Pub. Date: Jan. 15, 2004

(65) Prior Publication Data

US 2005/0283026 A1    Dec. 22, 2005

(30) Foreign Application Priority Data

Jul. 5, 2002    (ZA) ................. 2002/5387

(51) Int. Cl.
*C07F 15/00* (2006.01)
*B01J 31/00* (2006.01)
*C07C 2/26* (2006.01)

(52) U.S. Cl. .................. 556/22; 556/23; 502/155; 548/101; 526/171; 585/511; 585/514; 585/523

(58) Field of Classification Search ............... 556/22, 556/23; 502/155; 548/101; 526/171; 585/511, 585/514, 523
See application file for complete search history.

(56) References Cited

FOREIGN PATENT DOCUMENTS

| GB | 1 109 787 A | 4/1968 |
| WO | WO 00 58322 A | 10/2000 |
| WO | WO 02 14248 A | 2/2002 |

OTHER PUBLICATIONS

Fürstner; "Olefin Metathesis and Beyond"; Angew. Chem. Int. Ed. 2000, vol. 39, 2000, pp. 3012-3043, (2000).

Scholl, et al.; "Synthesis and Activity of a New Generation of Ruthenium-Based Olefin Metathesis Catalysts Coordinated with 1,3-Dimesityl-4,5-dihydroimidazol-2-ylidene Ligands"; Organic Letters, vol. 1, No. 6, pp. 953-956, (1999).

Trnka, et al.; "The Development of $L_2X_2R_u$=CHR Olefin Metathesis Catalysts: An Organometallic Success Story"; Accounts of Chemical Research; vol. 34, No. 1, pp. 18-29, (2001).

*Primary Examiner*—Porfirio Nazario-Gonzalez
(74) *Attorney, Agent, or Firm*—Finnegan, Henderson, Farabow, Garrett, & Dunner, L.L.P.

(57) ABSTRACT

The use of a phosphorus containing Ligand as a Ligand for a metathesis catalyst in a catalysed metathesis reaction wherein the phosphorus containing Ligand is a heterocyclic organic compound with a ligating phosphorus atom as an atom in the heterocyclic ring structure of the heterocyclic organic compound. The invention also relates to a metathesis catalyst such a phosphorus containing Ligand and to a metathesis reaction using the catalyst.

17 Claims, 4 Drawing Sheets

PHOSPHOROUS CONTAINING LIGANDS FOR METATHESIS CATALYSTS

TECHNICAL FIELD

The invention relates to the use of a phosphorus containing ligand in the preparation of a metathesis catalyst and to the use of a phosphorus containing ligand in a catalysed metathesis reaction. The invention also relates to a metathesis catalyst including such a phosphorus containing ligand and to a metathesis reaction using the catalyst.

BACKGROUND TO THE INVENTION

There is considerable interest regarding the formation of carbon-carbon bonds via olefin metathesis. Olefin metathesis (or disproportionation) refers to the metal-catalysed redistribution of carbon-carbon double bonds. Cross metathesis (CM) can be described as a metathesis reaction between two non-cyclic olefins, which may be the same or different, for example:

Where the olefins are the same, the reaction is known as self metathesis.

Ring-opening metathesis polymerization (ROMP) is a variant of olefin metathesis reactions wherein cyclic olefins (for example) produce polymers and co-polymers, for example:

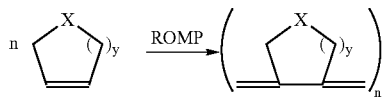

Ring-closing metathesis (RCM) represents a process in which an acyclic diene (for example) is cyclised to produce a cycloalkene, for example;

As indicated above metathesis reactions take place in the presence of a catalyst. A great deal of research has been done in an attempt to synthesise and isolate catalysts which are able to catalyse homogeneous olefin metathesis reactions. More particularly the synthesis of Group VIII transition metal metathesis catalysts has lead to catalysts with increased functional group tolerance and stability with respect to conditions such as air, water and acids.

During the 1990's the so-called "1$^{st}$ generation Grubbs catalyst" of formula 1a was developed:

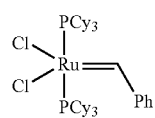

(1a)

where Cy is cyclohexyl.

This well defined ruthenium (Ru) alkylidene catalyst afforded high selectivities, high reaction rates and good tolerance for oxygenates in feed during homogeneous olefin metathesis reactions, including cross metathesis, ring closing metathesis and ring opening metathesis polymerisation. These processes have many potential commercial applications for the commodities, pharmaceutical and fine chemicals industries as well as in the field of speciality polymers. Several reviews describe the development and applications of Grubbs-type catalysts (for example Acc. Chem. Res. 2001, 34, 18–24; Angew. Chem., Int. Ed., 2000, 39, 3012–3043).

Much research has been carried out to investigate the effect of changing the nature of the ligands, (for example J. Am. Chem. Soc. 1997, 119, 3887–3897; Tetrahedron Lett. 1999, 40, 2247–2250; Angew. Chem., Int. Ed. 1998, 37, 2490–2493) resulting in the development of second generation Grubbs catalysts. The main thrust of second generation Grubbs catalyst research has related to a move away from the use of phosphine ligands to the use of highly nucleophilic N-heterocyclic carbenes for homogeneous metathesis reactions. Formula 1b shows the structure of the standard second generation Grubbs catalyst. While this catalyst shows greater reactivity compared to catalyst 1a, it is more expensive than the first generation catalyst.

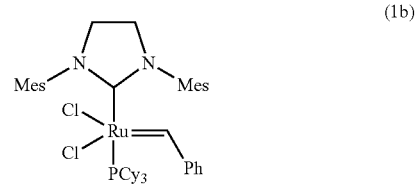

(1b)

where Cy=cyclohexyl and Mes=mesityl

In the case of hydroformylation reactions, research has continued into the use of phosphine ligands. It will be appreciated that in a hydroformylation process an olefinic feedstock is reacted with carbon monoxide and hydrogen at elevated temperatures and pressures in the presence of a hydroformylation catalyst to produce oxygenated products. The hydroformylation catalyst is selected according to the particular oxygenated products which are required from a particular olefinic feedstock and may typically be phosphine and/or phosphite ligand modified rhodium (Rh) or cobalt (Co) catalyst. Many different phosphine and phosphite ligands have been suggested in the past. For example U.S. Pat. No. 3,400,163 discloses bicyclic heterocyclic sec- and tert-phosphines of the general formula 1c and it is stated that these phosphines are useful in the hydroformylation of olefins.

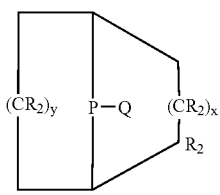

(1c)

U.S. Pat. No. 3,420,898 discloses olefin hydroformylation reactions in the presence of a cobalt catalysts with phosphine ligand of formula 1c.

Research has indicated that those phosphine ligands which appeared to lead to catalysts with higher selectivities and reaction rates In homogeneous metathesis reactions were often not suitable for the types of catalysts used in hydroformylation reactions, for example HCo(CO)$_3$P where P represents a phosphine ligand, for example tricyclohexyl phosphine (PCy$_3$).

However, it has now surprisingly been found that certain relatively inexpensive (compared to second generation Grubbs catalysts) phosphorus containing ligands such as phosphabicylononane ligands, which have been used in hydroformylation reactions, provide excellent stability, product yields and selectivities when used in a homogeneous metathesis catalyst. In addition, it has surprisingly been found that metathesis catalysts incorporating these phosphorus containing ligands in at least some cases show enhanced resistance to feed impurities. Furthermore, in at least some cases these catalysts afford superior performance for ring closing metathesis, ring opening metathesis polymerization and cross metathesis when compared to the standard first generation Grubbs catalyst (1a). When compared to the rather expensive standard second generation Grubbs catalyst (1b), in at least some cases their activity is comparable while the reaction selectivity is often superior.

SUMMARY OF THE INVENTION

According to a first aspect of the present invention there is provided the use of a phosphorus containing ligand as a ligand for a metathesis catalyst in a catalysed metathesis reaction wherein the phosphorus containing ligand is a heterocyclic organic compound with a ligating phosphorus atom as an atom in the heterocyclic ring structure of the heterocyclic organic compound.

According to a second aspect of the present invention there is provided the use of a phosphorus containing ligand in the preparation of a catalyst containing the ligand, which catalyst is for use in a metathesis reaction, wherein the phosphorus containing ligand is a heterocyclic organic compound with a ligating phosphorus atom as an atom in the heterocyclic ring structure of the heterocyclic organic compound.

According to a third aspect of the present invention there is provided a metathesis catalyst which includes a phosphorus containing ligand which is a heterocyclic organic compound with a ligating phosphorus atom as an atom in the heterocyclic ring structure of the heterocyclic organic compound.

Preferably the metathesis reaction is a homogenous metathesis reaction.

Preferably the ligating phosphorus atom is also bound to a further moiety which is not part of the heterocyclic ring structure.

Preferably the phosphorus containing ligand comprises a phosphine ligand, preferably a secondary or tertiary phosphine ligand, preferably a tertiary phosphine ligand. The further moiety bound to the ligating phosphorus atom may be an atom, and preferably it is H. In an alternative and preferred embodiment of the invention the said moiety may comprise an organyl. The organyl may comprise an alkyl, alkenyl, alkynyl, aryl, cycloalkyl, cycloalkenyl, cycloalkynyl and optionally it may be substituted. Preferably it comprises alkyl, cycloalkyl or aryl.

Preferably the heterocyclic organic compound has a single heteroatom in the form of the ligating phosphorus atom.

The heterocyclic organic compound may comprise a bicyclic organic compound. Preferably the heterocyclic organic compound includes no unsaturated carbon to carbon bonds. Preferably the two ring structures have at least 3 shared atoms. Preferably the two ring structures do not have more than 12 ring atoms, preferably they have nine ring atoms.

In a preferred embodiment of the invention the phosphine ligand comprises a bicyclic tertiary phosphine having a ligating phosphorus atom which is preferably bound to two first atoms (preferably carbon atoms) in the ring structure with each of said first atoms being bound to two other second atoms (preferably carbon atoms) in the ring structure. Preferably both the second atoms are carbon atoms.

It will be appreciated that in this embodiment each first atom is bound to three ring atoms.

In a preferred embodiment of the invention the heterocyclic organic compound comprises a phosphacycloalkane, preferably a phosphabicycloalkane, preferably a phosphabicyclononane, each of which optionally may be substituted. Preferably it comprises a monophosphacycloalkane, preferably a monophosphabicycloalkane, preferably a monophosphabicyclononane. Preferably the compound comprises a tertiary phosphine.

In a preferred embodiment of the invention, the phosphabicyclononane is a 9-phosphabicyclo[3.3.1]nonane of formula 2a or a 9-phosphabicyclo[4.2.1] nonane of formula 2b or mixtures thereof:

(2a)

(2b)

wherein R$_1$ is H or an organyl. Preferably R$_1$ is an optionally substituted alkyl, or optionally substituted aryl, or an optionally substituted cycloalkyl.

The phosphabicyclononane may be a compound of formula 2a.

In one embodiment of the invention R$_1$ is alkyl, preferably —C$_{20}$H$_{41}$ also known as eicosyl. In this instance the ligand is known as eicosyl phoban (that is for both compounds of formula 2a and 2b where R$_1$ is —C$_{20}$H$_{41}$).

In one preferred embodiment of the invention R$_1$ is cyclohexyl. In this instance the ligand is known as cyclohexyl phoban (that is for both compounds of formula 2a and 2b where R$_1$ is cyclohexyl).

The catalyst or metathesis catalyst may comprise a transition metal based catalyst, preferably a group VIII metal based catalyst, preferably a Ru based catalyst. The catalyst may include ligands as defined below.

The metathesis reaction may comprise cross metathesis (including self metathesis and ethenolysis), ring-opening metathesis polymerisation or ring-closing metathesis.

According to another aspect of the present invention there is provided a compound of formula 3:

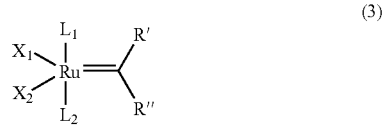

(3)

wherein
  L₁ is a neutral electron donor ligand;
  L₂ is a phosphorous containing ligand in the form of a heterocyclic organic compound with a ligating phosphorus atom as an atom in the heterocyclic ring structure of the heterocyclic organic compound;
  X₁ and X₂ are independently selected from an anionic ligand; and
  R' and R" are independently selected from H or an organyl.

Preferably the compound is a catalyst, preferably a metathesis catalyst, and preferably a homogeneous metathesis catalyst.

Ligand L₁

L₁ may be selected from the group consisting of phosphine, sulfonated phosphine, phosphite, phosphinite, phosphonite, arsine, stibine, amine, amide, imine, nitrosyl, carbene and pyridine. In a preferred embodiment of the invention L₁ may be any neutral phosphine ligand or carbene ligand. Preferably L₁ is a phosphine preferably a phosphine of the formula PR³R⁴R⁵, wherein R³, R⁴ and R⁵ are each independently aryl, C₁–C₁₀ alkyl or cycloalkyl. Preferably L₁ is selected from the group consisting of —P(cyclohexyl)₃; —P(cyclopentyl)₃; —P(iso-propyl)₃; and —P(phenyl)₃. Preferably it comprises a neutral phosphine ligand as defined in respect of 4. Accordingly L₁ may be the same as L₂.

In another embodiment of the invention L₁ may be selected from a group of heterocyclic compounds containing substituted or unsubstituted five membered rings which may be saturated or unsaturated and which may include at least two adjacent or non adjacent nitrogen atoms as part of the group. Examples of such ligands are illustrated as formulas 4, 5 and 6:

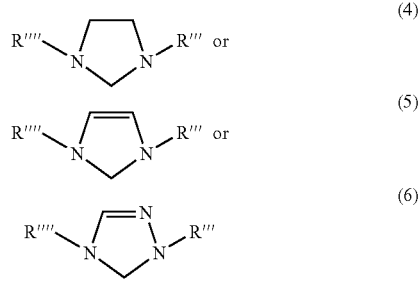

(4)

(5)

(6)

wherein R'" and R"" may be any group such as H or an organyl, including alkyl, aryl, cycloalkyl, adamantyl or the like, and may be further substituted with functional groups.

Ligand L₂

L₂ is preferably a phosphorus containing ligand as already described above. Namely, the phosphorus containing ligand may comprises a phosphine ligand, preferably a secondary or tertiary phosphine ligand, preferably a tertiary phosphine ligand. The ligating phosphorus atom may also be bound to a further moiety which is not part of the heterocyclic ring structure. The further moiety bound to the ligating phosphorus atom may be an atom, and preferably it is H. In an alternative and preferred embodiment of the invention the said moiety may comprise an organyl. The organyl may comprise an alkyl, alkenyl, alkynyl, aryl, cycloalkyl, cycloalkenyl, cycloalkyenyl and optionally it may be substituted. Preferably it comprises alkyl, cycloalkyl or aryl.

Preferably the heterocyclic organic compound has a single heteroatom in the form of the ligating phosphorus atom.

The heterocyclic organic compound may comprise a bicyclic organic compound. Preferably the heterocyclic organic compound includes no unsaturated carbon to carbon bonds. Preferably the two ring structures have at least 3 shared atoms. Preferably the two ring structures do not have more than 12 ring atoms, preferably they have nine ring atoms.

In a preferred embodiment of the invention the phosphine ligand comprises a bicyclic tertiary phosphine having a ligating phosphorus atom which is preferably bound to two first atoms (preferably carbon atoms) in the ring structure with each of said first atoms being bound to two other second atoms (preferably carbon atoms) in the ring structure. Preferably both the second atoms are carbon atoms. It will be appreciated that in this embodiment each first atom is bound to three ring atoms.

In a preferred embodiment of the invention the heterocyclic organic compound comprises a phosphacycloalkane, preferably a phosphabicycloalkane, preferably a phosphabicyclononane, each of which optionally may be substituted. Preferably it comprises a monophosphacycloalkane, preferably a monophosphabicycloalkane, preferably a monophosphabicyclononane. Preferably the compound comprises a tertiary phosphine.

In a preferred embodiment of the invention, the phosphabicyclononane is a 9-phosphabicyclo-[3.3.1]nonane of formula 2a or a 9-phosphabicyclo[4.2.1] nonane of formula 2b or mixtures thereof:

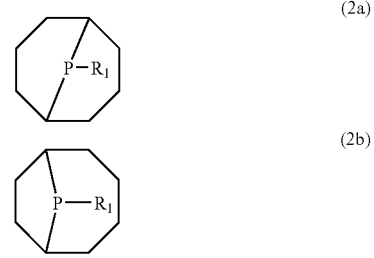

(2a)

(2b)

wherein R₁ is H or an organyl. Preferably R₁ is an organyl, preferably an optionally substituted alkyl, or optionally substituted. aryl, or an optionally substituted cycloalkyl. The phosphabicyclononane may be a compound of formula 2a.

In one embodiment of the invention the organyl comprises alkyl, preferably —C₂₀H₄₁ also known as eicosyl. In this instance the ligand is known as eicosyl phoban (that is for both compounds of formula 2a and 2b where R₁ is —C₂₀H₄₁).

In one preferred embodiment of the invention R₁ is cyclohexyl. In this instance the ligand is known as cyclohexyl phoban (that is for both compounds of formula 2a and 2b where R₁ is cyclohexyl.

Ligands $X_1$ and $X_2$ $X_1$ and $X_2$ may be independently selected from hydrogen; halide; or a compound selected from the group consisting of $C_1$–$C_{20}$ alkyl; aryl; $C_1$–$C_{20}$ alkoxide; aryloxide; $C_3$–$C_{20}$ alkyldiketonate; aryldiketonate; $C_1$–$C_{20}$ carboxylate; arylsulfonate; $C_1$–$C_{20}$ alkylsulfonate; $C_1$–$C_{20}$ alkylthiol; aryl thiol; $C_1$–$C_{20}$ alkylsulfonyl; and $C_1$–$C_{20}$ alkylsulfinyl, the compound being optionally substituted with one or more other moieties selected from the group consisting of $C_1$–$C_{10}$ alkyl; $C_1$–$C_{10}$ alkoxy; aryl and halide. Preferably $X_1$ and $X_2$ are each independently selected from the group consisting of halide; $CF_3CO_2$; $CH_3CO_2$; $CFH_2CO_2$; $(CH_3)_3CO$; $(CF_3)_2(CH_3)CO$; $(CF_3)(CH_3)_2CO$; PhO; MeO; EtO; tosylate; mesylate; and trifluoromethanesulfonate. Preferably $X_1$ and $X_2$ are each independently selected from halide. Preferably $X_1$ and $X_2$ are each chloride.

Substituents R' and R"

R' and R" are each independently selected from hydrogen or an organyl selected from the group consisting of $C_1$–$C_{20}$ alkyl; $C_2$–$C_{20}$ alkenyl; $C_2$–$C_{20}$ alkynyl; aryl; $C_1$–$C_{20}$ carboxylate; $C_1$–$C_{20}$ alkoxy; $C_2$–$C_{20}$ alkenyloxy; $C_2$–$C_{20}$ alkynyloxy; aryl; $C_2$–$C_{20}$ alkoxycarbonyl; $C_1$–$C_{20}$ alkylthiol; aryl thiol; $C_1$–$C_{20}$ alkylsulfonyl and $C_1$–$C_{20}$ alkylsulfinyl, the organyl being optionally substituted with one or more moieties preferably selected from the group consisting of $C_1$–$C_{10}$ alkyl; $C_1$–$C_{10}$ alkoxy; aryl; and a functional group selected from the group consisting of hydroxyl; thiol; thioether; ketone; aldehyde; ester; ether; amine; imine; amide; nitro; carboxylic acid; disulfide; carbonate; isocyanate; carbodiimide; carboalkoxy; carbamate; and halogen. Preferably R' is hydrogen and R" is phenyl or vinyl, optionally substituted with one or more moieties selected from the group consisting of $C_1$–$C_5$ alkyl; $C_1$–$C_5$ alkoxy; phenyl; and a functional group selected from the group consisting of hydroxyl; thiol; thioether; ketone; aldehyde; ester; ether; amine; imine; amide; nitro; carboxylic acid; disulfide; carbonate; isocyanate; carbodiimide; carboalkoxy; carbamate; and halogen. Preferably R' is H and R" is phenyl or —C═C(CH$_3$)$_2$.

In some cases some of the ligands $X_1$, $X_2$, $L_1$, $L_2$, R' and R" may be linked to each other, for example:

$L_1$ to $X_1$ for example to form a bidentate Schiff base ligand such as:

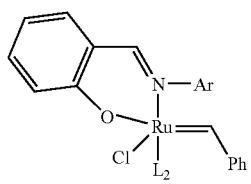

wherein $L_2$ is as defined above.

In a preferred embodiment of the invention, the catalyst may be of the structure of formula 7, wherein $L_2$ is the same or different and is as defined above. Preferably $L_2$ are the same and preferably $L_2$ is a phosphabicyclononane ligand. In a preferred embodiment $L_2$ may be a 9-phosphabicyclononane ligand of formula 2a or 2b. Preferably $L_2$ is cyclohexyl phoban.

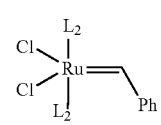

(7)

In another preferred embodiment of the invention, the catalyst may be of the structure of formula 8, wherein $L_2$ is the same or different and is as defined above. Preferably $L_2$ are the same and preferably $L_2$ is a phosphabicyclononane ligand. In a preferred embodiment $L_2$ may be a 9-phosphabicyclononane ligand of formula 2a or 2b. Preferably $L_2$ is cyclohexyl phoban.

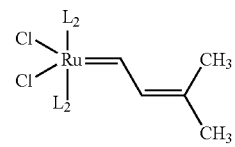

(8)

According to another aspect of the invention there is provided the use of a catalyst of formula 3 above in a metathesis reaction, preferably a homogeneous metathesis reaction.

The reaction is preferably a homogeneous metathesis reaction of preferably at least one olefinic compound and the reaction conditions for the metathesis reaction wherein the catalyst of formula 3 is used may be in accordance to conditions which are well known to a person skilled in the art of metathesis reactions.

The at least one olefinic compound may comprise an olefin with one or more double bonds or a compound which includes an olefinic moiety with one or more double bonds. Preferably the olefinic compound has a single double bond in the case of a cross-metathesis reaction. Preferably the olefinic compound has two double bonds in the case of a ring-closing metathesis reaction. Preferably the olefinic compound is a cyclic olefin in the case of a ring-opening metathesis polymerisation reaction.

According to a further aspect of the invention there is provided a metathesis product produced by a metathesis reaction using a catalyst substantially as described hereinabove.

The metathesis catalyst may be a Grubbs catalyst of formula 3 hereinbefore, preferably a homogeneous metathesis catalyst.

According to yet a further aspect of the invention there is provided a catalysed metathesis reaction wherein at least one olefinic compound is subjected to metathesis in the presence of a catalyst of the type described hereinbefore. Preferably the metathesis reaction is a homogeneous metathesis reaction.

According to yet a further aspect of the invention there is provided a process for a ring closing metathesis reaction in the presence of a catalyst of the type described hereinbefore. According to yet a further aspect of the invention there is provided a process for a ring opening metathesis polymerization reaction in the presence of a catalyst of the type described hereinbefore. According to yet a further aspect of the invention there is provided a process for a cross or self metathesis reaction in the presence of a catalyst of the type described hereinbefore. The cross metathesis reaction may specifically be an ethenolysis reaction (where one of the two olefinic compounds is ethylene). The metathesis reactions preferably comprise homogeneous metathesis reactions.

The process may further be characterised therein that the catalyst may be formed in situ. The process may then include the steps of adding together sufficient quantities of a source of ruthenium which may be an inorganic salt of ruthenium e.g. $RuCl_3 \cdot xH_2O$, a source of ligand in the form of $L_2$ described above, a precursor which would form the carbene structure on the central Ru atom for example an alkyne like butynedioldiacetate and a requisite starting material for the metathesis reaction.

Without thereby limiting the scope of the invention it will now be further described with reference to the following examples.

EXAMPLE 1

In Situ Formed Catalysis

This example is in respect of the homogeneous metathesis of 1-octene to form 7-tetradecene using an in situ formed catalyst system with a ruthenium concentration of 100 ppm. The comparison is between the phosphine ligands eicosyl phoban (EP) and $PCy_3$ as ligands in an in situ formed metathesis catalyst.

General Experimental Procedure:

Reactions were carried out in a 100 ml three-necked flask fitted with a reflux condenser, thermometer and septum. The reflux condenser was connected to a cooling bath to ensure a constant flow of chilled water through the jacket, thereby preventing loss of octene. The top of the condenser was connected to a cold trap and bubbler in order to monitor liquid losses and gas emissions. The thermometer was positioned below the level of the reaction solution to ensure correct temperature monitoring. The reaction flask was purged with argon to ensure removal of oxygen. The reagents [EP or $PCy_3$, $RuCl_3 \cdot xH_2O$ and 1,4-butynedioldiacetate (BDD) and 1-octene)] were added to the flask under inert conditions, then a slow hydrogen sparge (2 bubbles per second) was started and maintained during the reaction. The reaction mixture was heated, with stirring, to the desired temperature. Samples were taken at regular intervals with a syringe through the septum and quenched with a mixture of toluene and two drops of t-butylhydroperoxide. Samples were analyzed by GC using a Pona column. Unless otherwise stated, 20 ml of octene was employed in all experiments, and catalyst, solvent and additive amounts were calculated relative to this. Octadecane in an amount of 0.5 ml was used as internal standard. The conversion percentages (as molar %) of 1-octene to 7-tetradecene are provided in FIGS. 1 and 2.

1.1 Comparison of EP and $PCy_3$ as Ligands in the Metathesis Reaction at 50° C.

Figure 1:
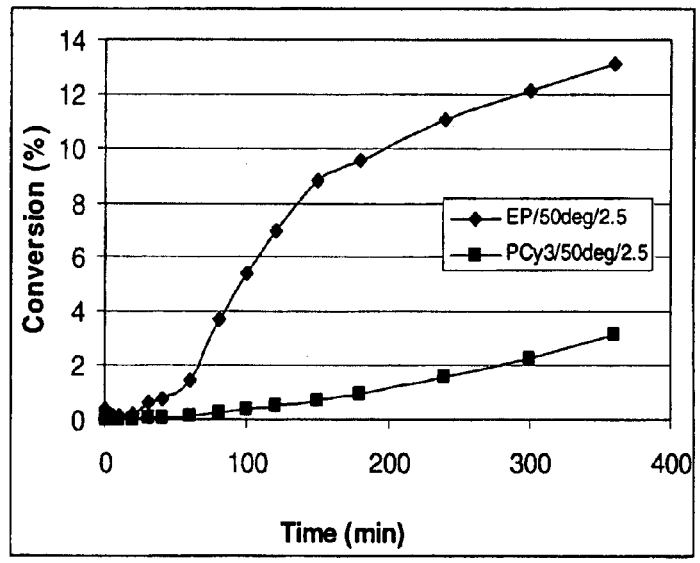
FIG. 1 is a graph showing the comparison of the percentage conversion of EP and $PCY_3$ in a metathesis reaction carried out at 50° C.

It is evident from the graph in FIG. 1 that EP performs far better than $PCy_3$ at 50° C., affording higher reaction rates and conversions.

Reaction Conditions:
100 ppm Ru
2.5:1 phosphine ligand:ruthenium (molar ratio)
10:1 BDD:Ru (molar ratio)
T=50° C.

1.2 Comparison of EP and $PCy_3$ as Ligands in the Metathesis Reaction at 110° C.

Figure 2:
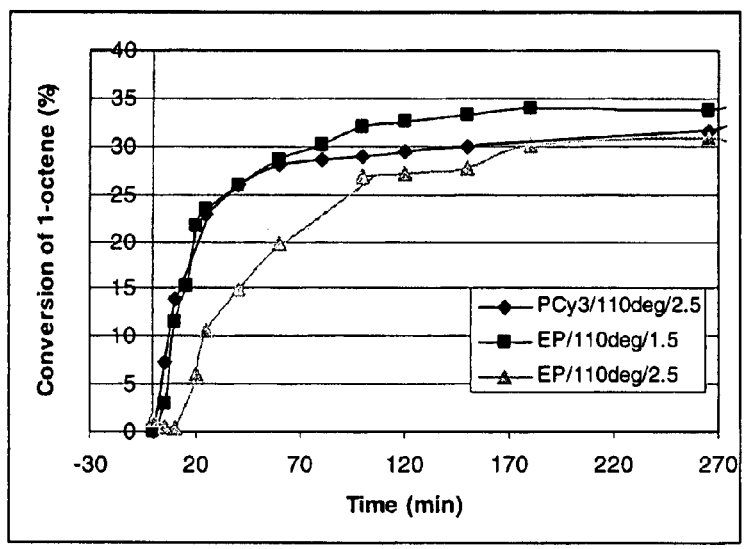
FIG. 2 is a graph showing the comparison of the percentage conversion of EP and $PCY_3$ in a metathesis reaction carried out at 110° C.

It is evident from the graph in FIG. 2 that at high temperatures, EP shows similar reaction rates and affords higher yields at lower ligand concentrations (1.5:1 molar ratio for EP versus 2.5:1 molar ratio for $PCy_3$).

Reaction Conditions:
100 ppm Ru
2.5:1 and 1.5:1 phosphine ligand:ruthenium (molar ratio)
10:1 BDD:Ru (molar ratio)
T=110° C.

At higher temperatures with a 2:5 molar ratio of phosphine ligand to ruthenium, $PCy_3$ affords improved reaction rates compared to the corresponding EP reaction which is slower. However EP catalyst stability is sustained over a far longer period, and the end of run conversions are the same for both. This suggests that EP coordinates more strongly to the metal center, thereby giving added catalyst stability but slowing reaction rates as phosphine dissociation is hindered.

[According to the generally accepted reaction mechanism, phosphine dissociation is required before metathesis can proceed].

In order to further explore this, less ligand was added (EP or $PCy_3$: Ru molar ratio of 1.5:1). In the case of $PCy_3$ [not shown] lower ligand concentrations led to poorer yields of the desired metathesis product, presumably due to lower catalyst stabilities. However in the case of EP, lower ligand concentrations afforded improved reaction rates and yields. Thus at 110° C., only 1.5 equivalents of EP are required to get similar reaction rates and improved yields of desired product relative to those obtained with 2.5 equivalents of $PCy_3$. The reduced amount of ligand required allows a tremendous reduction in process costs.

EXAMPLE 2

Preformed Catalysts

Preparation of Cyclohexyl Phoban is as Follows:

A 3-neck round bottomed flask equipped with pressure-equalising dropping funnel was charged with 1,5-cyclooctadiene (de-oxygenated, 5.3 mL, 4.663 g, $4.31 \times 10^{-2}$ mols) and cyclohexylphosphine (6.0 mL, 5.250 g, $4.52 \times 10^{-2}$ mols) and heated to 105° C. A toluene (d/d/d, 20 ml) solution of VAZO® (VAZO®=1,1'-Azobis(cyclohexanecarbonitrile; 3 g) was then added dropwise to the vigorously stirred solution over 2 hours and the solution heated at 105° C. for a further 21 hours. At this point a further 0.5 g of VAZO® (as a solid) was added to the reaction mixture and heating continued for a further 8 hours. After this time the volatiles were removed in vacuo to leave a viscous, pale yellow, oil.

The oil was subjected to a short-path distillation (fraction distilling at >96° C. collected) to leave a white, waxy solid (analysis showed this to be contaminated with VAZO decomposition products). This solid was then subjected to a Kugelrohr distillation and the fraction distilling at ~110° C. recovered (4.570 g, 47% as a white, waxy solid). The ligand was isolated as a 3:1 mixture of [3.3.1] and [4.2.1] isomers; 31P NMR (C6D6): 13.6, −25.3 ppm. That is cyclohexyl phoban formed, that is the compound of formula 2a and 2b wherein $R_1$ is cyclohexyl.

The catalysts were prepared according to the following reaction scheme. Complex B was prepared using the known literature method of Fogg et al [D. Amoroso, J. L. Snelgrove, J. C. Conrad, S. D. Drouin, G. P. A. Yap and D. E. Fogg, *Adv. Sythn. Catal.*, 2002, 344, 757].

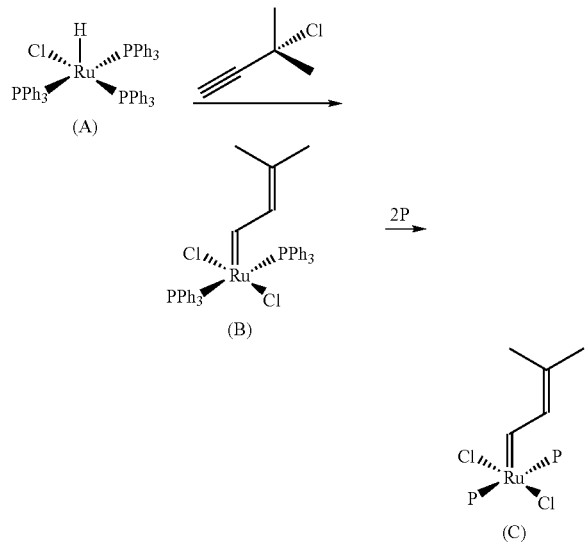

Figure 3:
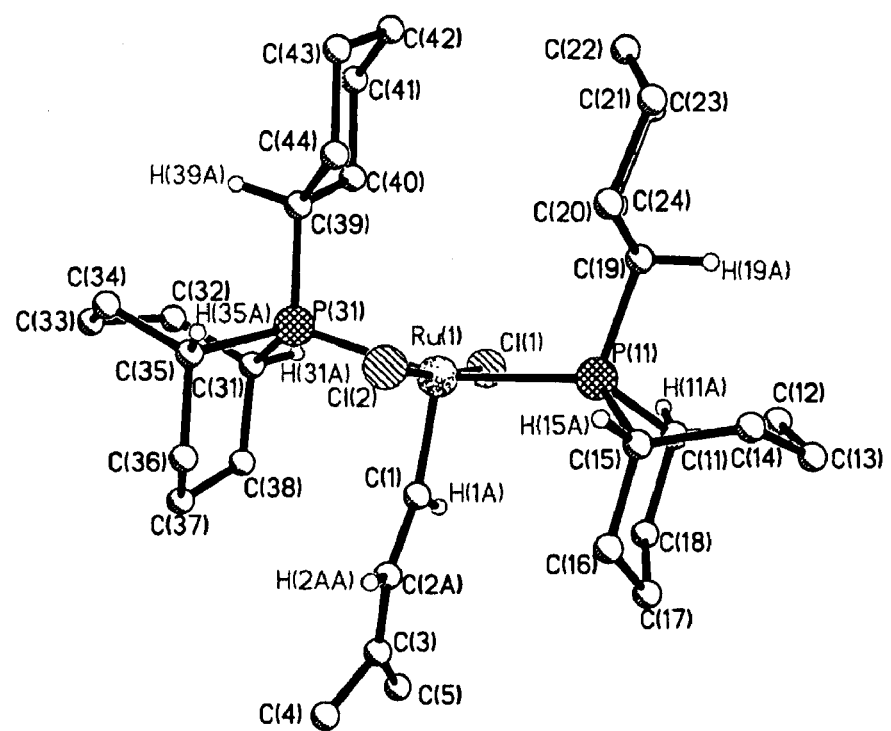
FIG. 3 is a representation of The X-ray crystal structure for the complex of Example 2.

A specific procedure for preparation of the compound of formula 8 wherein $L_2$ is cyclohexyl phoban from complex B via this route is as follows:

A solution of cyclohexyl phoban (0.65 mmol) in $CH_2Cl_2$ (10 ml) was added dropwise to complex (B) (0.26 mmol) in $CH_2Cl_2$ (10 ml) and stirred overnight at room temperature. The solution turned from dark brown to purple. The solvent was removed in vacuo followed by the addition of petroleum ether (20 ml). The solution was cooled to −15° C. to precipitate the product of formula 8 wherein $L_2$ is cyclohexyl phoban as a purple solid (0.14 mmol, 55% yield). $^{31}P$ NMR (121.4 MHz, $CD_2Cl_2$) δ 22 (very broad); $^1H$ NMR (300 MHz, $CD_2Cl_2$) δ 19.6 (d, Ru═CH, 1H, $^3J_{HH}$=11.52 Hz), 8.2 (d, Ru═CHCH, 1H, $^3J_{HH}$=11.7 Hz). $^{13}C$NMR (75.4 MHz, $CD_2Cl_2$) δ 284 (m, Ru═C). The X-ray crystal structure for this complex is shown in FIG. 3. Selected bond length and angle data is shown in the Table 1.

TABLE 1

| Bond lengths [Å] and angles [°] for the compound of FIG. 3 | |
|---|---|
| Bond | Lengths and Angles |
| Ru(1)—C(1) | 1.795(7) |
| Ru(1)—P(11) | 2.3834(16) |

TABLE 1-continued

| Bond lengths [Å] and angles [°] for the compound of FIG. 3 | |
|---|---|
| Bond | Lengths and Angles |
| Ru(1)—P(31) | 2.3842(17) |
| Ru(1)—Cl(1) | 2.3983(17) |
| Ru(1)—Cl(2) | 2.4025(16) |
| C(1)—Ru(1)—P(11) | 99.6(2) |
| C(1)—Ru(1)—P(31) | 98.2(2) |
| P(11)—Ru(1)—P(31) | 162.23(6) |
| C(1)—Ru(1)—Cl(1) | 93.0(3) |
| P(11)—Ru(1)—Cl(1) | 90.24(6) |
| P(31)—Ru(1)—Cl(1) | 88.36(6) |
| C(1)—Ru(1)—Cl(2) | 93.3(3) |
| P(11)—Ru(1)—Cl(2) | 88.94(6) |
| P(31)—Ru(1)—Cl(2) | 90.50(6) |
| Cl(1)—Ru(1)—Cl(2) | 173.66(7) |

One possible preparation of such catalysts where the alkylidene is specifically a benzylidene group (that is a compound of (formula 7), involves the displacement of tricyclohexyl phosphine ($PCy_3$) from the standard first generation Grubbs catalyst (1a). A specific example for the preparation of the benzylidene complex of formula 7 (wherein $L_2$ is cyclohexyl phoban) is as follows:

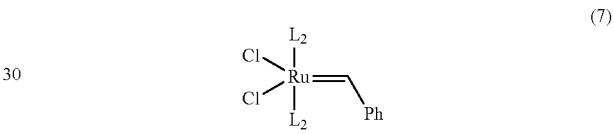

(7)

To a suspension of the Grubbs catalyst of formula 1a (10 mmol) and cyclohexyl phoban (40 mmol) was added degassed DCM (15 ml). After stirring at room temperature for 16 h, the solvent was removed, and degassed pentane was added to the residue. The mixture was sonicated for 1 min, and the solid filtered. To the solid was added degassed cold MeOH. The suspension was sonicated again for 1 min and filtered. The complex of formula 7 wherein $L_2$ is cyclohexyl phoban was isolated as a purple solid (5.8 mmol, 58%). $^1H$ NMR (300 MHz, $d^8$ Toluene): 20.2 ppm (s, 1H, Ru═CH), 9.7 ppm (bs, 1H, o-H of $C_6H_5$), 7.5 ppm (bs, 1H, o-H of $C_6H_5$), 7.1 ppm (t, $^3J_{HH}$=7.6 Hz, p-H of $C_6H_5$), 2.6 ppm (4H, P—C—H of Phoban), 2.20–0.70 ppm (m, 46H). $^{31}P$ NMR (121 MHz, $d^8$ Toluene): 24 ppm (bs). Mass Spec: (TOF MS ES+); 733.728 (M+Na)$^+$, 710.74 (M$^+$).

Catalysis Experiments with Preformed Catalysts

The performance of the novel catalysts was compared with the standard first generation Grubbs catalyst (1a) and in some cases with the standard second generation catalyst (1b) in homogeneous metathesis reactions.

2.1 Ring Closing Metathesis with Compound 7 ($L_2$=Cyclohexyl Phoban)

Reactions were carried out in a 250 ml three-necked flask fitted with a reflux condenser, thermometer and septum. A needle inserted through the septum and connected to a gas supply via a needle valve was used to ensure a slow and steady stream of argon through the reaction solution. Dry, degassed toluene (80 ml) was added, followed by diethyl-diallylmalonate (4 g 16.8 mmol) and the reaction was heated at 50° C. The catalyst of formula 7 wherein $L_2$ is cyclohexyl phoban (0.01 mmol) was weighed into a custom-made aluminum weighing tray and added to the reaction mixture.

Figure 4:
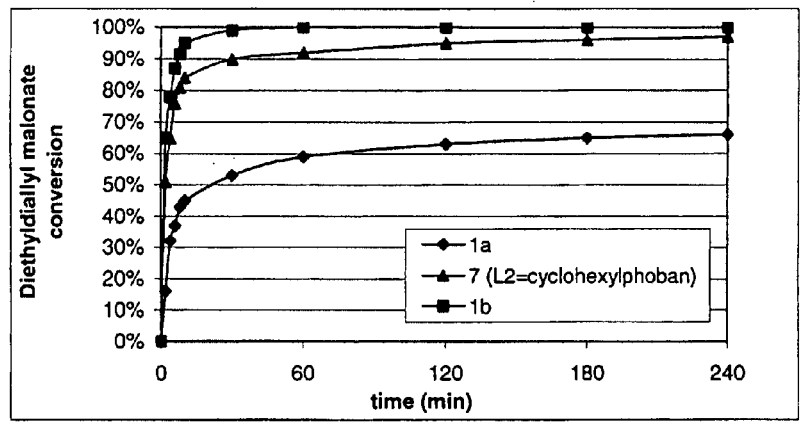
FIG. 4 is a graph wherein the percentage conversion of diethyldiallyl malonate in a ring closing metathesis reaction is compared with reference to a standard first generation Grubb's catalyst (1a); a standard second generation Grubb's catalyst (1b) and the catalyst of the invention, namely a catalyst of formula 7.

Samples were taken at regular intervals via syringe through the septum. Samples were analysed by GC with a Pona column using an FID. Results are shown in FIG. 4.

It is evident that the catalyst of formula 7 ($L_2$=cyclohexyl phoban) performs ring-closing metathesis of diethyldiallyl-malonate to form cyclopent-3-ene-1,1-dicarboxylic acid diethyl ester (at a substrate to catalyst molar ratio of 1680/1, 50 deg, 0.01 M in toluene) significantly faster than the catalyst of formula 1a and compares favourably to results obtained with the much more expensive catalyst of formula 1b.

2.2 Ring Opening Metathesis Polymerization with Compound 7 ($L_2$=Cyclohexyl Phoban)

Figure 5:
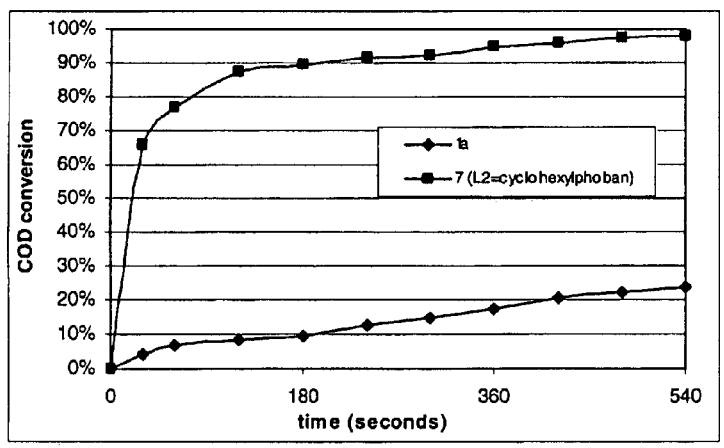
FIG. 5 is a graph wherein the percentage conversion of COD in a ring opening metathesis reaction is compared with reference to a standard first generation Grubb's catalyst (1a) and the catalyst of the invention, namely a catalyst of formula 7.

Into a glass vial was added 2 ml of dry, degassed toluene, followed by decane (900 µl, internal standard for GC) COD (0.46 g, 4.63 mmol) was added, followed by toluene. A solution of catalyst (0.001838 mmol) in toluene (100 µl) was added and the reaction was monitored by GC by taking samples at regular intervals. Results are shown FIG. 5.

It is clear that the catalyst of formula 7 ($L_2$=cyclohexyl phoban) catalyses ROMP of 1,5-cyclooctadiene (COD) to form 1,4-polybutadiene faster than the catalyst for formula 1a at a substrate to catalyst molar ratio (S/C) of 2500/1)

2.3 Cross Metathesis with Compound 7 ($L_2$=Cyclohexyl Phoban)

2.3.1 1-Decene Metathesis, 65° C.

Figure 6:
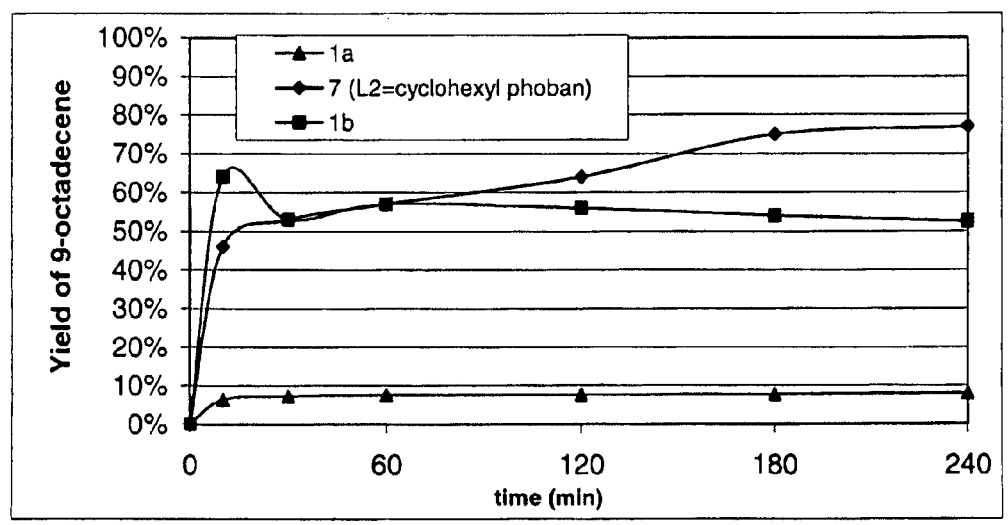
FIG. 6 is a graph wherein the yield of 9-octadene from 1-decene in a cross metathesis reaction is compared with reference to a standard first generation Grubb's catalyst (1a); a standard second generation Grubb's catalyst (1b) and the catalyst of the invention, namely a catalyst of formula 7.

Reactions were carried out in a 250 ml three-necked flask fitted with a reflux condenser, thermometer and septum. A needle inserted through the septum and connected to a gas supply via a needle valve was used to ensure a slow and steady stream of argon through the reaction solution. Dry, degassed 1-decene (24 ml) was added, and the reaction was heated at 65° C. The catalyst (0.014 mmol) was weighed into a custom-made aluminum weighing tray and added to the reaction mixture. Samples were taken at regular intervals via syringe through the septum. Samples were analysed by GC using a Pona column. Results are shown in FIG. 6.

Under identical conditions, the catalyst of formula 1a showed a poor performance, for the 1-decene metathesis to 9-octadecene while the catalyst of formula 1 b showed lower final yields of the desired product due to extensive formation of side products. The catalyst of formula 7 ($L_2$=cyclohexylphoban) gave the highest yield of desired product.

2.3.2 1-Octene Metathesis, 50 Degrees.

Reactions were carried out in a 100 ml three-necked flask fitted with a reflux condenser, thermometer and septum. A needle Inserted through the septum and connected to a gas supply via a needle valve was used to ensure a slow and steady stream of argon through the reaction solution. Dry, degassed 1-tene (20 ml) was added, and the reaction was heated at 50° C. The catalyst (0.014 mmol) was weighed into a custom-made aluminum weighing tray and added to the reaction mixture. Samples were taken at regular intervals via syringe through the septum. Samples were analysed by GC using a Pona column. Results are shown in the Table 2 below.

TABLE 2

| | Product Yield (molar %) | |
|---|---|---|
| Time (min) | Catalyst 1a | Catalyst 7 ($L_2$ = cyclohexyl phoban) |
| 120 | 34% | 57% |
| 360 | 34% | 84% |

Complex 7 ($L_2$=cyclohexylphoban) efficiently catalyses the self-metathesis of 1-octene to 7-tetradecene, affording significantly higher yields under the same conditions as 1a. Under the reaction conditions, little visible decomposition is observed, and conversions are significantly higher than those achievable with commercial Grubbs $1^{st}$ generation catalyst of formula 1a. It is evident that catalyst 1a decomposes within the first two hours of reaction, as no further product formation is observed, while complex 7 ($L_2$=cyclohexyl phoban) shows activity over at least 6 hours. Thus complex 7 ($L_2$=cyclohexyl phoban) has a superior catalyst lifetime.

2.3.3 Ethenolysis of 2-Octene

A 50 ml Parr autoclave was fitted with a 50 ml addition vessel connected via a needle valve to the autoclave diptube. The autoclave was sealed and thoroughly flushed with ethylene. 2-Octene (16.5 ml) was introduced to the addition vessel via syringe. It was then introduced to the autoclave by applying 10 bar of ethylene pressure to the addition vessel and opening the needle valve on the diptube. Stirring (1000 rpm) was started immediately, and the reactor contents were heated to 45° C. The catalyst (0.018 mmol) was dissolved in the octane (8.5 ml), and when the reactor contents were at the desired temperature, the catalyst solution was introduced to the autoclave by applying 15 bar of ethylene pressure to the addition vessel and opening the needle valve on the diptube. Once the reactor pressure had stabilised, the needle valve was closed and the reaction was stirred at 45° C. for 2 hours. Samples were taken at intervals and monitored by GC using a Pona column. Results are shown in Table 3 below.

TABLE 3

| | 2-octene conversion (molar %) | |
|---|---|---|
| Time (min) | Catalyst 1a | Catalyst 7 $L_2$ = cyclohexyl phoban) |
| 20 | 17% | 27% |
| 40 | 17% | 38% |
| 120 | 18% | 45% |

It is evident that complex 7 ($L_2$=cyclohexylphoban) affords faster reaction rates and higher conversions than catalyst 1a for the reaction of 2-octene and ethylene to form 1-heptene. Catalyst activity is also sustained over a longer period with complex 7 ($L_2$=cyclohexyl phoban).

2.3.4 Cross Metathesis of Sasol 1-Heptene Feed

Fischer-Tropsch-derived olefins contain a multitude of impurities which have a deleterious effect on many homogeneous catalysts. A Fischer-Tropsch (FT) derived $C_7$ feed with the following composition was employed (percentages expressed as molar %):

| Linear 1-alkene | 86% |
|---|---|
| Linear internal alkene | 1–1.5% |
| Branched alkene (incl. internal) | 5–7% |
| Cyclic alkene | 1–2% |
| Diene | 1% |
| Oxygenate | <100 ppm |
| Paraffins, aromatics & other | 5–7% |

Reactions were carried out in a 100 ml three-necked flask fitted with a reflux condenser, thermometer and septum. A needle inserted through the septum and connected to a gas supply via a needle valve was used to ensure a slow and steady stream of argon through the reaction solution. Dry, degassed 1-heptene feed (20 ml) was added, and the reaction was heated at 50° C. The catalyst (0.014 mmol) was then added as a solid to the preheated reaction mixture. Samples were taken at intervals via syringe through the septum. Samples were analysed by GC using a Pona column. Results are shown in Table 4 below.

TABLE 4

| | 1-heptene conversion (molar %) | |
| --- | --- | --- |
| Time (min) | Catalyst 1a | Catalyst 7 ($L_2$ = cyclohexyl phoban) |
| 20 | 19% | 39% |
| 60 | 19% | 52% |
| 360 | 19% | 70% |

It is evident from these results that complex 7($L_2$=cyclohexyl phoban) affords far superior results to catalyst 1a for the metathesis of a Fischer Tropsch derived 1-heptene feed to form 6-dodecene. It is also clear that catalyst 1a is poisoned very quickly by trace impurities, as it shows no further conversion of substrate after 20 minutes, and does not reach the conversion obtained with pure 1-octene feed (34%). In comparison, complex 7 ($L_2$=cyclohexyl phoban) affords much higher conversions of substrate, and catalyst activity is maintained over a longer period. The catalyst therefore shows a greater tolerance to feed impurities.

2.4 Cross Metathesis of 1-Octene with Complex 8 ($L_2$=Cyclohexyl Phoban)

Reactions were carried out in a 250 ml three-necked flask fitted with a reflux condenser, thermometer and septum. A needle inserted through the septum and connected to a gas supply via a needle valve was used to ensure a slow and steady stream of argon through the reaction solution. Dry, degassed 1-octene (20 ml) was added, and the reaction was heated at 50° C. The catalyst (0.014 mmol) was weighed into a custom-made aluminum weighing tray and added to the reaction mixture. Samples were taken at regular intervals via syringe through the septum. Samples were analysed by GC using a Pona column. Results are shown in Table 5 below.

TABLE 5

| | Product Yield (molar %) | |
| --- | --- | --- |
| Time (min) | Catalyst 1a | Catalyst 8 ($L_2$ = cyclohexyl phoban) |
| 120 | 34% | 44% |
| 360 | 35% | 82% |

It is evident from these results that complex 8 ($L_2$=cyclohexyl phoban) affords superior results to catalyst 1a for the metathesis of 1 octene to 7-tetradecene.

From the above examples it can be seen that catalysts including ligands according to the present invention and catalysts according to the present invention may have improved performance over the prior art catalysts in at least one of the following aspects:
  i) higher reaction rates;
  ii) higher conversions;
  iii) improved catalyst stability;
  iv) improved rates/yields at lower ligand concentrations; and
  v) higher yields of desired products.

It will be appreciated that many variations in detail are possible without thereby departing from the spirit and scope of the invention.

The invention claimed is:

1. A metathesis catalyst comprising a phosphorus containing ligand which is a heterocyclic organic compound in the form of a phosphabicycloalkane with a ligating phosphorus atom as an atom in the heterocyclic ring structure of the heterocyclic organic compound.

2. A compound of formula 3:

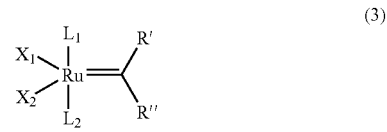

(3)

wherein
  $L_1$ is a neutral electron donor ligand;
  $L_2$ is a phosphorous containing ligand in the form of a heterocyclic organic compound in the form of a phosphabicycloalkane with a ligating phosphorus atom as an atom in the heterocyclic ring structure of the heterocyclic organic compound;
  $X_1$ and $X_2$ are independently an anionic ligand; and
  R' and R'' are independently H or an organyl.

3. The compound of claim 2 which is a homogeneous metathesis catalyst.

4. The compound of claim 2 wherein $L_1$ is the same as $L_2$.

5. The compound of claim 2 wherein the phosphorus containing ligand of $L_2$ comprises a phosphine ligand.

6. The compound of claim 5 wherein $L_2$ is a 9-phosphabicyclo[3.3.1]nonane, of formula 2a, or a 9-phosphacicyclo[4.2.1]nonane of formula 2b or mixtures thereof:

(2a)

(2b)

wherein $R_1$ is H or an organyl.

7. The compound of claim 6 wherein $R_1$ is —$C_{20}H_{41}$.

8. The compound of claim 6 wherein $R_1$ is cyclohexyl.

9. The compound of claim 2 wherein $X_1$ and $X_2$ are each a halide.

10. The compound of claim 2 which is a compound of formula 7.

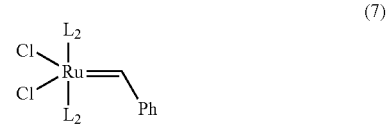

(7)

wherein $L_2$ is the same or different.

11. The compound of claim 2 which is a compound of formula 8

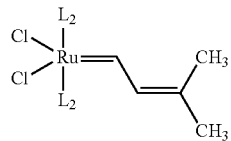

(8)

wherein L$_2$ is the same or different.

12. The compound of claim 10 wherein L$_2$ is a 9-phosphabicyclo[3.3.1]nonane, of formula 2a, or a 9-phosphabicyclo[4.2.1]nonane of formula 2b or mixtures thereof:

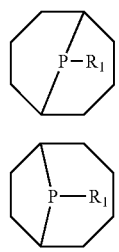

(2a)

(2b)

wherein R$_1$ is H or an organyl.

13. A catalysed metathesis reaction comprising subjecting at least one olefinic compound to metathesis in the presence of a compound of formula 3:

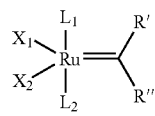

(3)

wherein

L$_1$ is a neutral electron donor ligand;

L$_2$ is a phosphorous containing ligand in the form of a heterocyclic organic compound in the form of a phosphabicycloalkane with a ligating phosphorus atom as an atom in the heterocyclic ring structure of the heterocyclic organic compound;

X$_1$ and X$_2$ are independently an anionic ligand; and

R' and R" are independently H or an organyl.

14. The catalysed metathesis reaction of claim 13 wherein the compound of formula 3 is formed in situ.

15. The compound of claim 11 wherein L$_2$ is a 9-phosphabicyclo[3.3.1]nonane, of formula 2a, or a 9-phosphabicyclo[4.2.1]nonane of formula 2b or mixtures thereof:

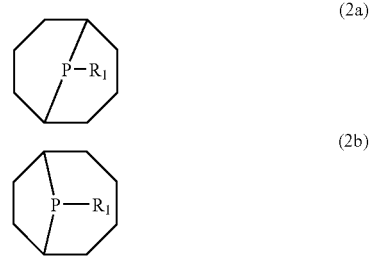

(2a)

(2b)

wherein R$_1$ is H or an organyl.

16. A catalysed metathesis reaction comprising subjecting at least one olefinic compound to metathesis in the presence of a metathesis catalyst comprising a phosphorus containing ligand which is a heterocyclic organic compound in the form of a phosphabicycloalkane with a ligating phosphorous atom as an atom in the heterocyclic ring structure of the heterocyclic organic compound.

17. The catalysed metathesis reaction of claim 13 or 16, wherein the metathesis reaction is a homogeneous metathesis reaction selected from the group consisting of cross-metathesis, ring-opening metathesis polymerization and ring closing metathesis.

* * * * *

UNITED STATES PATENT AND TRADEMARK OFFICE
CERTIFICATE OF CORRECTION

PATENT NO. : 7,276,616 B2 Page 1 of 1
APPLICATION NO. : 10/518716
DATED : October 2, 2007
INVENTOR(S) : Catherine Lynn Dwyer et al.

It is certified that error appears in the above-identified patent and that said Letters Patent is hereby corrected as shown below:

Claim 6, column 16, line 36, "9-phosphacicyclo" should read --9-phosphabicyclo--.

Signed and Sealed this

Eighteenth Day of December, 2007

JON W. DUDAS
*Director of the United States Patent and Trademark Office*